United States Patent

Römer

[11] 4,354,976
[45] Oct. 19, 1982

[54] PROCESS FOR THE PREPARATION OF AZIDOBENZAL COMPOUNDS

[75] Inventor: Michael Römer, Rodgau, Fed. Rep. of Germany

[73] Assignee: Merck Patent Gesellschaft mit Beschränkter Haftung, Darmstadt, Fed. Rep. of Germany

[21] Appl. No.: 218,250

[22] Filed: Dec. 19, 1980

[30] Foreign Application Priority Data

Dec. 19, 1979 [DE] Fed. Rep. of Germany ....... 2951101

[51] Int. Cl.³ .......................................... C07C 117/00
[52] U.S. Cl. ..................................... 260/349; 564/306
[58] Field of Search ......................... 260/349; 564/306

[56] References Cited

U.S. PATENT DOCUMENTS 2,940,853  6/1960  Sagura et al. ................... 260/349 X

FOREIGN PATENT DOCUMENTS 2064597  7/1972  Fed. Rep. of Germany ... 260/349 X
2245518  4/1973  Fed. Rep. of Germany ... 564/306 X Primary Examiner—Joseph Paul Brust
Attorney, Agent, or Firm—Millen & White

[57] ABSTRACT

A process for preparing a 2,6-bis-[(4-azidophenyl)methylene]-cyclohexanone of the formula

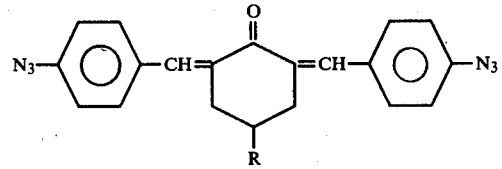

wherein R is hydrogen or alkyl of 1–6 C atoms, comprises condensing a cyclohexanone of the formula

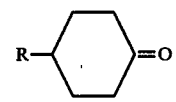

wherein R is as defined above, with 4-aminobenzaldehyde, the 4-amino group optionally being protected, in the presence of an alkaline condensing agent; removing the protective group when the 4-amino group is protected; diazotizing the resultant 2,6-bis-[(4-aminophenyl)methylene]-cyclohexanone of the formula

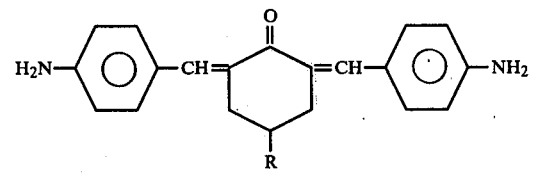

wherein R is as defined above, and reacting the diazotization product with an alkali metal azide.

3 Claims, No Drawings

PROCESS FOR THE PREPARATION OF AZIDOBENZAL COMPOUNDS

BACKGROUND OF THE INVENTION

The present invention relates to a new process for preparing azidobenzal compounds.

Aromatic azido compounds are of industrial importance as crosslinking agents for coatings crosslinkable by light and which consist of certain polymeric compounds, for example photoresists based on cyclized polyisoprenes.

The 2,6-bis-[(4-azidophenyl)-methylene]-cyclohexanones of formula I

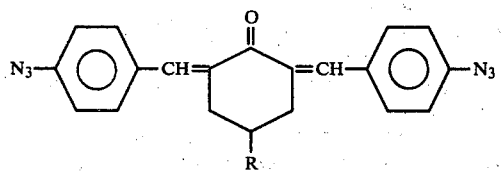

wherein R is hydrogen or alkyl of 1–6 C atoms, are particularly frequently used as such crosslinking agents. Various processes are already known for their preparation, but they all have considerable disadvantages.

For example, according to U.S. Pat. No. 2,940,853, 4-azidobenzaldehyde is subjected to a condensation reaction with a cyclohexanone of formula (II)

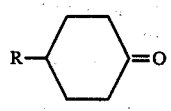

wherein R is as defined above. However, since 4-azidobenzaldehyde is an exceptionally explosive substance, its use requires extensive and expensive safety measures. According to German Offenlegungsschrift No. 2,064,597, the use of 4-azidobenzaldehyde can be avoided by subjecting 4-nitrobenzaldehyde to a condensation reaction with a cyclohexanone of formula (II). The nitro groups in the resulting 2,6-bis-[(4-nitrophenyl)-methylene]-cyclohexanones, which are likewise explosive, are then selectively reduced to amino groups. The latter are then converted into azido groups using conventional methods, by diazotization and reaction with sodium azide. In this process, hydrazine hydrate in the presence of Raney nickel is used for the selective reduction of the nitro groups. This process is also unsuitable for the preparation of 2,6-bis-[(4-azidophenyl)methylene]-cyclohexanones of formula (I) on an industrial scale because of the large amounts of Raney nickel required for the reduction.

SUMMARY OF THE INVENTION

Accordingly, it is an object of this invention to provide a new process by which 2,6-bis-[(4-azidophenyl)-methylene]-cyclohexanone can be prepared easily and in good yield on an industrial scale.

Upon further study of the specification and appended claims, further objects and advantages of this invention will become apparent to those skilled in the art.

These objects have been attained, in one aspect, by this invention based on the surprising finding, that 2,6-bis-[(4-azidophenyl)-methylene]-cyclohexanones of formula (I) can be prepared in good yields on an industrial scale when 4-aminobenzaldehyde or a derivative thereof protected on the amino group is subjected to a condensation reaction with a cyclohexanone of the formula (II) in the presence of an alkaline condensing agent and the 2,6-bis-[(4-aminophenyl)-methylene]-cyclohexanone thus obtained, if appropriate after removal of the protective groups, of formula (III)

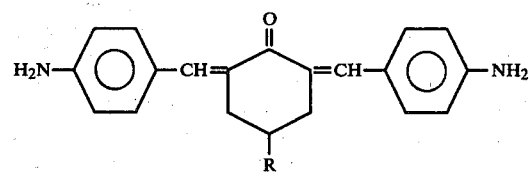

wherein R is as defined for formula (I), is diazotized and the diazotization product is reacted with an alkali metal azide.

DETAILED DISCUSSION

The condensation of the 4-aminobenzaldehyde with the cyclohexanone, which proceeds smoothly, is particularly surprising since, in view of the processes known hitherto, it was to be expected that an electron-withdrawing substituent such as the nitro group in the 4-position of the benzaldehyde would favor the condensation, while an electron-donating substituent such as the amino group should inhibit it. Moreover, it was to be expected that a considerable proportion of the 4-aminobenzaldehyde would be lost by self-condensation under the reaction conditions, and that the products of this side reaction would make working up of the reaction mixture more difficult. Surprisingly, this is not the case.

4-aminobenzaldehyde of any origin can in principle be employed in the process of this invention. However, to optimize the applicability of this process to commercialization, it should be determined whether the material is already substantially contaminated by products of self-condensation. These can interfere considerably with the working up of the product reaction mixture. In such cases, it has proved expedient to isolate the 4-aminobenzaldehyde from the crude source by preparing a derivative protected on the amino group by a customary protective group, as discussed above. Suitable protective groups of this type include, in principle, all those which are sufficiently stable under the conditions of the condensation reaction and which, nevertheless, can easily be split off subsequently, for example, benzoyl and, in particular, acetyl. See, e.g. Houben-Weyl-Müller, Methoden der Organischen Chemie (G. Thieme Verlag, Stuttgart, 4th Edition 1958), Volume XI/2, Pages 3–37, which is incorporated by reference herein. In a preferred embodiment of the process of this invention, however, 4-aminobenzaldehyde which has been freshly prepared in a conventional manner from 4-nitrotoluene by reaction with sodium sulfide and sulfur in aqueous-alcoholic sodium hydroxide solution, is employed without purification.

The other starting materials for the process of this invention, i.e., the cyclohexanones of formula (II), are known and can be obtained in a sufficiently pure form.

The condensation reaction is carried out in a manner which is in itself conventional. Suitable alkaline condensing agents include, in particular, alkali metal hydroxides and alkali metal alcoholates; aqueous sodium hydroxide solution which contains 20-60 g of sodium hydroxide in 100 ml of solution is preferably used. Aliphatic alcohols of 1-4 C atoms are preferably used as the reaction medium, but ethers, such as diethyl ether, tetrahydrofuran or anisole, or polar solvents, such as dimethylformamide, can also be employed.

The condensation reaction is carried out at a temperature between room temperature and the boiling point of the reaction medium. Lower temperatures, in particular up to about 50° C., are generally used if a 4-aminobenzaldehyde protected on the amino group is employed.

The condensation reaction is generally concluded after 2 to 24 hours. The longer reaction times are as a rule necessary for the reaction of a 4-aminobenzaldehyde unprotected on the amino group. In general the amounts of the various components are, e.g., 2-3 moles of the 4-aminobenzaldehyde and 0.02-0.5 moles of the alkaline reagent per mole of cyclohexanone II, the concentration of the latter in the starting reaction medium generally being 0.2-4 moles/l.

The diazotization of the 2,6-bis-[(4-aminophenyl)-methylene]-cyclohexanone of the formula (III) and the subsequent reaction with an alkali metal azide, in particular sodium azide, are carried out in a manner which is known from the literature, by adding first an aqueous sodium nitrite solution and then a sodium azide solution to a solution of the amino compound in aqueous hydrochloric acid, while cooling. The 2,6-bis-[(4-azidophenyl)-methylene]-cyclohexanone of formula (I) thereby separates out in crystalline form and is usually sufficiently pure, after filtration, washing with water and drying, to be used as a crosslinking agent in photoresists. In a few exceptional cases, if particularly high demands are made with regard to the degree of purity of the product, the product can be recrystallized from acetone or another suitable solvent in a manner which is in itself conventional, if necessary, using active charcoal.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) 880 ml of water, 66 g of sodium sulfide, 59.4 g of sodium hydroxide and 33 g of powdered sulfur are added to a slightly warmed solution of 110 g of 4-nitrotoluene in 440 ml of methanol and the mixture is heated under reflux to the boiling point for 3 hours. Unreacted 4-nitrotoluene is then distilled off with steam and the 4-aminobenzaldehyde which crystallizes out on cooling is filtered off and dissolved in 160 ml of isopropanol. After adding 9 g of aqueous sodium hydroxide solution (50% NaOH) and 24 g of 4-methylcyclohexanone, the reaction mixture is heated under reflux to the boiling point for 16 hours. After cooling, the 2,6-bis-[(4-aminophenyl)-methylene]-4-methylcyclohexanone which has crystallized out is filtered off and washed with hot water; yield: 37 g, m.p. 251°.

The following compounds are prepared analogously:
2,6-bis-[(4-aminophenyl)-methylene]-cyclohexanone, m.p. 186°,
2,6-bis-[(4-aminophenyl)-methylene]-4-ethylcyclohexanone,
2,6-bis-[(4-aminophenyl)-methylene]-4-n-propylcyclohexanone,
2,6-bis-[(4-aminophenyl)-methylene]-4-isopropylcyclohexanone,
2,6-bis-[(4-aminophenyl)-methylene-4-n-butylcyclohexanone,
2,6-bis-[(4-aminophenyl)-methylene]-4-isobutylcyclohexanone,
2,6-bis-[(4-aminophenyl)-methylene]-4-tert-butylcyclohexanone,
2,6-bis-[(4-aminophenyl)-methylene]-4-n-pentylcyclohexanone,
2,6-bis-[(4-aminophenyl)-methylene]-4-neopentylcyclohexanone,
2,6-bis-[(4-aminophenyl)-methylene]-4-(2-methylbutyl)-cyclohexanone and
2,6-bis-[(4-aminophenyl)-methylene]-4-n-hexylcyclohexanone.

(b) A solution of 10 g of sodium nitrite in 20 ml of water and a solution of 9.8 g of sodium azide in 34 ml of water are successively added dropwise to a solution of 25 g of 2,6-bis-[(4-aminophenyl)-methylene]-4-methylcyclohexanone in 126 ml of 18% hydrochloric acid, while stirring and cooling to 5%. The 2,6-bis-[(4-azidophenyl)-methylene]-4-methylcyclohexanone which has precipitated is filtered off, washed thoroughly with water and recrystallized from acetone; yield: 22 g, m.p. 129° (with decomposition).

The following compounds are prepared analogously:
2,6-bis-[(4-azidophenyl)-methylene]-cyclohexanone, m.p. 144° (decomposition),
2,6-bis-[(4-azidophenyl)-methylene]-4-ethylcyclohexanone,
2,6-bis-[(4-azidophenyl)-methylene]-4-n-propylcyclohexanone,
2,6-bis-[(4-azidophenyl)-methylene]-4-isopropylcyclohexanone,
2,6-bis-[(4-azidophenyl)-methylene]-4-n-butylcyclohexanone,
2,6-bis-[(4-azidophenyl)-methylene-4-isobutylcyclohexanone,
2,6-bis-[(4-azidophenyl)-methylene-4-tert-butylcyclohexanone,
2,6-bis-[(4-azidophenyl)-methylene]-4-n-pentylcyclohexanone,
2,6-bis-[(4-azidophenyl)-methylene]-4-neopentylcyclohexanone,
2,6-bis-[(4-azidophenyl)-methylene]-4-(2-methylbutyl)-cyclohexanone and
2,6-bis-[(4-azidophenyl)-methylene]-4-n-hexylcyclohexanone.

EXAMPLE 2

(a) 50 g of crude 4-aminobenzaldehyde is stirred in 143 g of acetic anhydride at 30°-45° for 20 hours. The reaction mixture is then evaporated to a volume of about 70 ml under reduced pressure and cooled to −5° and the 4-acetaminobenzaldehyde which has crystallized out is filtered off and dried in vacuo; yield: 53.5 g, m.p. 153°-155°.

(b) 6.4 g of 32% aqueous sodium hydroxide solution and 6.4 g of water are added to a solution of 32.6 g of 4-acetaminobenzaldehyde and 11.2 g of 4-methylcyclohexanone in 110 ml of isopropanol and the mixture is stirred at 30°-40° for 3 hours. It is then cooled to 10° and the 2,6-bis-[(4-acetaminophenyl)-methylene]-4- methylcyclohexanone which has crystallized out is filtered off and dried in vacuo; yield: 30.1 g, m.p. 260°–263°.

(c) 30.1 g of 2,6-bis-[(4-acetaminophenyl)-methylene]-4-methycyclohexanone, 60 g of 32% aqueous sodium hydroxide solution and 210 ml of isopropanol are heated to the boiling point for 24 hours. After cooling, the 2,6-bis-[(4-aminohenyl)-methylene]-4-methylcyclohexanone which has crystallized out is filtered off, washed with hot water and dried; Yield: 21.2 g, m.p. 250°–251.5°.

(d) 2,6-bis-[(4-aminophenyl)-methylene]-4-methylcyclohexanone is reacted with sodium nitrite and sodium azide analogously to Example 1 to give 2,6-bis-[(4-azidophenyl)-methylene]-4-methylcyclohexanone.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a 2,6-bis-((4-azidophenyl)-methylene)-cyclohexanone of the formula

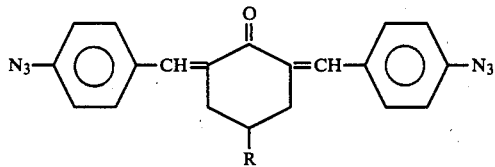

wherein R is hydrogen or alkyl of 1–6 C atoms, comprising
   (a) freshly preparing 4-aminobenzaldehyde by reacting 4-nitrotoluene with sodium sulfide and sulfur in aqueous-alcoholic sodium hydroxide solution and removing unreacted 4-nitrotoluene, whereby there is produced 4-aminobenzaldehyde substantially uncontaminated by products of self-condensation;
   (b) directly after step (a), condensing the residual 4-aminobenzaldehyde, without purification, with a cyclohexanone of the formula

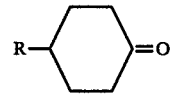

wherein R is as defined above, in the presence of an alkaline condensing agent, whereby there is prepared a 2,6-bis-((4-aminophenyl)-methylene)-cyclohexanone of the formula

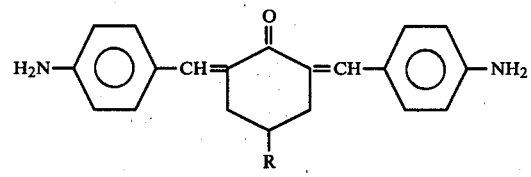

wherein R is as defined above, which is substantially uncontaminated by products derived from the self condensation of 4-aminobenzaldehyde; and
   (c) diazotizing the 2,6-bis-((4-aminophenyl)-methylene)-cyclohexanone product and reacting the diazotization product with an alkali metal azide.

2. A process of claim 1 wherein the alkaline condensing agent is NaOH.

3. A process of claim 1 wherein the reaction temperature is from room temperature to the boiling point of the reaction medium.

* * * * *